United States Patent [19]

Kruse et al.

[11] Patent Number: 4,734,502

[45] Date of Patent: Mar. 29, 1988

[54] PROCESS FOR THE PREPARATION OF 2,2,6,6-TETRAMETHYL-4-OXOPIPERIDINE

[75] Inventors: Walter M. Kruse, Wilmington, Del.; John F. Stephen, West Chester, Pa.

[73] Assignee: ICI Americas Inc., Wilmington, Del.

[21] Appl. No.: 944,835

[22] Filed: Dec. 22, 1986

[51] Int. Cl.$^4$ .......................................... C07D 211/74
[52] U.S. Cl. .................................................. 546/242
[58] Field of Search ........................................ 546/242

[56] References Cited

U.S. PATENT DOCUMENTS

| | | | |
|---|---|---|---|
| 3,513,170 | 5/1970 | Murayama et al. | 546/242 |
| 3,953,459 | 4/1976 | Orban et al. | 546/242 |
| 3,959,295 | 5/1976 | Orban et al. | 435/14 |
| 3,959,298 | 5/1976 | Murayama et al. | 546/242 |
| 3,960,875 | 6/1976 | Orban et al. | 546/242 |
| 3,963,730 | 6/1976 | Murayama et al. | 546/242 |
| 4,252,958 | 2/1981 | Hirai et al. | 546/242 |
| 4,275,211 | 6/1981 | Orban et al. | 546/242 |
| 4,356,308 | 10/1982 | Wiezer et al. | 546/242 |
| 4,536,581 | 8/1985 | Cantatore et al. | 546/242 |

FOREIGN PATENT DOCUMENTS

| | | | |
|---|---|---|---|
| 74607 | 3/1983 | European Pat. Off. | 546/242 |
| 0152934 | 2/1985 | European Pat. Off. | 546/242 |
| 2916471 | 11/1980 | Fed. Rep. of Germany | 546/242 |
| 2176777 | 1/1987 | United Kingdom | 540/240 |

OTHER PUBLICATIONS

Chem. Abstracts, vol. 85(5), Abstract No. 32863e, (1976).
Chem. Abstracts, vol. 86(7), Abstract No. 43562c, (1977).
Chem. Abstracts, vol. 91(23), Abstract No. 193188c, (1979).
Chem. Abstracts, vol. 92(19), Abstract No. 163844s, (1980).
Chem. Abstracts, vol. 92(3), Abstract No. 22386g, (1980).
Chem. Abstracts, vol. 95(3), Abstract No. 24824j, (1981).
Sosnovsky et al., "Prep. Triacetoneamine", *Z. Naturforsch* 32b, 328–337 (1977).
Matter, "Uber ein Neues Reaction Product aus Acetone und Ammonia", *Helv. Chim. Acta, XXV*, 1114–1122 (1947).

*Primary Examiner*—Henry R. Jiles
*Assistant Examiner*—Zinna Northington

[57] ABSTRACT

2,2,6,6-tetramethyl-4-oxopiperidine is prepared from acetone and ammonia in the presence of catalytic amounts of active halogen compounds selected from sulfonylhalides, sulfurylhalides, N-haloamides, N-haloimides, β-haloesters, α-haloketones, α-halohydroxy compounds, and β-halonitriles.

2 Claims, No Drawings

PROCESS FOR THE PREPARATION OF 2,2,6,6-TETRAMETHYL-4-OXOPIPERIDINE

The present invention is directed to an improved process for synthesis of 2,2,6,6-tetramethyl-4-oxopiperidine. It is directed to a process for producing 2,2,6,6-tetramethyl-4-oxopiperidine directly from acetone and ammonia at low temperatures and pressures. Specifically it is directed to reacting acetone with ammonia in the presence of novel catalysts. Such catalysts are selected from compounds with active halogens selected from alkyl and aryl derivatives of sulfonylhalides, haloamides, haloimides, $\beta$-haloesters, $\beta$-halonitriles, $\alpha$-halohydroxy compounds and $\beta$-haloketones and sulfurylhalides.

Conventional synthesis for the preparation of 2,2,6,6-tetramethyl-4-oxypiperdine(triacetonamine) involves the reaction of excess acetone with ammonia in the presence of a Lewis acid at low temperatures to form acetonine as an intermediate which is thereafter hydrolyzed at higher temperatures. Acetonine is formed in the first step at room temperature and transformed to triacetonamine at 50°–70° C. Triacetonamine is isolated by distillation in up to 85% yields or by precipitation with water as a hydrate in up to 73% yields.

We have now found that a group of active halogen compounds can be used in place of prior art catalysts to improve the reaction speed and increase yields at lower temperatures and pressures. The process comprises two stages which can be performed one immediately after the other in the same reactor so that it is particularly suitable for large scale commercial manufacture of a tetramethylpiperidine product. The process according to the invention is carried out as follows:

a. Acetone is reacted with ammonia at concentrations of (0.5–1.5 mol NH$_3$ per mol acetone) in the presence of 0.01–0.1 mol (of an active halogen catalyst) per mol of acetone used at 5° to 30° C., and thereafter b. With additional acetone in concentrations of (5–10 mols acetone per mol NH$_3$) by further heating at 50°–70° C.

As catalysts may be employed: sulfonyl halides R—SO$_2$X; sulfuryl halides SO$_2$X$_2$; N-haloimides RCO—N(X)—COR: N-haloamides RCO(NHX): $\beta$-haloesters RCH(X)(CH$_2$)—CO$_2$R; $\beta$-halonitriles RCH(X)CH$_2$—CN; $\alpha$-haloalcohols RC(OH)—CH$_2$X; and $\alpha$-haloketones RCO—CH$_2$(X) wherein X is chlorine or bromine and R is selected from hydrocarbyl radicals selected from alkyl, aralkyl, alkylaryl groups having up to 22 carbon atoms. Such compounds include tetrachloro1,4-benzoquinone, methanesulfonylchloride, sulfurylchloride, 1,3-dibromo-5,5-dimethylhydantoin, 1,3-dichloro-5,5-dimethylhydantoin, N-bromosuccinimide, trichloromelamine, trichloroisocyanuric acid, 3-chloropropionitrile, ethyl-3-chloropropionate, 1,3-dichloro-2-propanol, and N-chlorsuccinimide and the chloro or bromo equivalents.

The first stage of the reaction is carried out at temperatures of about 25°–30° C. at atmospheric pressure. The second stage is then carried out with the addition of acetone at temperatures of 50°–70° C.

The practice of the process of the invention can better be understood by reference to the following non-limiting examples wherein all proportions are expressed in parts by weight unless otherwise specified.

EXAMPLE 1

Into a one liter bottle provided with rubber liner, steel crown cap and magnetic stirrer were placed 7.4 g (0.0375 mol) 1,3-dichloro-5,5-dimethylhydantion and 135 g acetone. The crown cap was equipped with a small opening through which a needle was inserted for evacuation or injection of liquids. A water aspirator vacuum was applied for a few minutes and the bottled weighed. After evacuations 21 g ammonia was introduced within 1 hour at 20° C. After an additional 2 hours at room temperature 300 g acetone was added and the temperature raised to 67° C. for 4 hours and continued to react over night at 56° C. According to gas chromatographic determination the reaction solution contained 138 g, 2,2,6,6-tetramethyl-4-oxopiperidinehydrate. To this solution was added 20 g sodium hydroxide and stirred for 1 hour. The two phases were separated and 270 g acetone and low boiling by products were recovered by fractional distillation at 30°–84° C. under 15 mm Hg pressure to recover acetone, mesityl oxide, diacetone alcohol acetonine and a few grams of triacetonamine. In another cut (boiling point 84°–88° C. at 15 mm Hg) the product was recovered for a yield of 84.2% (based on used acetone).

EXAMPLE 2

According to a procedure and equipment outlined for Example 1, 10.7 g (0.0375 mol) 1,3-dibromo-5,5-dimethylhydantion and 135 g acetone were placed into the 1 liter bottle. 20.5 g ammonia were taken up within 3 hours. After addition of 300 g acetone, reaction mixture was kept at 67° C. for 8 hours. The yield determined by gas chromatographic techniques was determined to be 78.1% (based on used acetone).

EXAMPLE 3

According to the procedure outlined for Example 1, 4.3 g (0.0375 mol) methanesulfonylchloride and 135 g acetone and 21 g ammonia was added to the reactor. The reaction was continued at room temperature for 1.5 hours. After addition of 300 g acetone reaction was continued at 56° C. for 16 hours. The yield determined by gas chromatographic technique was 81.5% (based on used acetone).

EXAMPLE 4

According to the procedure of Example 1, 4.3 g (0.0375 mol) methanesulfonylchloride and 435 g (7.5 mol) acetone and 21 g ammonia were introduces into the reactor and placed in a water bath at 69° C. and kept there for 10 hours. After the similar recovery procedure of Example 1 the yield of 80.8% (based on used acetone) was obtained.

EXAMPLE 5

Employing the procedure of Example 1, 13.3 g (0.075 mol) N-bromosuccinimide gave a yield of 83.5% (based on used acetone).

EXAMPLE 6

According to the procedure of Example 1, 10.2 g (0.075 mol) ethyl-3-chloroproprionate and 21 g ammonia gave a yield of 81.8% (based on used acetone).

EXAMPLE 7

According to the procedure of Example 1, 7.0 g (0.075 mol) 3-chloropropionitrile and 22 g ammonia produced a yield of 79.7% (based on used acetone).

EXAMPLE 8

According to the procedure of Example 1, 3 g (0.045 mol) sulfurylchloride and 21 g ammonia produced a yield of 84.4% (based on used acetone).

What is claimed is:

1. In a process for the preparation of 2,2,-6,6-tetramethyl-4-oxopiperidine which comprises reacting acetone with ammonia at temperatures ranging from 5°–70° C. the improvement which comprises carrying out said reaction in the presence of catalytic amounts of active halogen compounds selected from those in the group consisting of $SO_2X_2$, $R-SO_2X$, $RCO-N(X)-COR$, $RCO(NHX)$, $RCH(X)CH_2-CO_2R$, $RCH(X)CH_2-CN$, $RCH(OH)-CH_2X$, and $RCO-CH_2(X)$ wherein X is chlorine or bromine and R is a group selected from alkyl, aryl, arylalkyl and alkylaryl groups having up to 22 carbon atoms wherein acetone is first reacted with ammonia in concentrations of 0.5–1.5 mol $NH_3$ per mol acetone at temperatures in the range of 5°–30° C., and there after with additional acetone in concentrations of 5–10 mols acetone per mol $NH_3$ at temperatures of 50°–70° C.

2. A process for the preparation of 2,2,6,6-tetramethyl-4-oxopiperidine which comprises reacting acetone with ammonia at temperatures ranging from 5°–70° C., the improvement which comprises carrying out said reaction in the presence of catalytic amounts of active halogen compounds selected from the group consisting of tetrachloro-1,-4-benzoquinone, methanesulfonylchloride, sulfurylchloride, 1,3-dibromo-5,5-dimethylhydantoin, 1,3-dichloro-5,5-dimethylhydantoin, N-bromosuccinimide, trichloromelamine, trichloroisocyanuric acid, 3-chloropropionitrile, ethyl-3-chloropropionate, 1,3-dichloro-2-propanol, and N-chlorosuccinimide and their chloro or bromo equivalents wherein acetone is first reacted with ammonia in concentration of 0.5–1.5 mol ammonia per mol acetone at temperatures in the range of 5°–30° C., and thereafter with additional acetone in concentrations of 5–10 mols acetone per mol ammonia at temperatures of 50°–70° C.

* * * * *